United States Patent
Campagnoli

(12) 
(10) Patent No.: US 6,800,597 B2
(45) Date of Patent: Oct. 5, 2004

(54) COSMETIC BATH COMPOSITION BASED ON HERBS AND A FOAMING AGENT, AND PACKAGING CONTAINING THE SAID COMPOSITION

(75) Inventor: Antonio Campagnoli, Piacenza (IT)

(73) Assignee: Zeca S.r.l., Piacenza (IT)

( * ) Notice: Subject to any disclaimer, the term of this patent is extended or adjusted under 35 U.S.C. 154(b) by 0 days.

(21) Appl. No.: 10/170,547

(22) Filed: Jun. 14, 2002

(65) Prior Publication Data

US 2003/0114325 A1 Jun. 19, 2003

(30) Foreign Application Priority Data

Dec. 17, 2001 (IT) ...................................... PC2001A0040

(51) Int. Cl.$^7$ ............................................... B61K 17/00
(52) U.S. Cl. ...................... 510/130; 510/139; 510/297; 424/401; 424/402; 424/404
(58) Field of Search ................................ 424/401, 402, 424/404, 466, 195.1, 489; 510/130, 446

(56) References Cited

U.S. PATENT DOCUMENTS

| 5,948,439 A | * | 9/1999 | Forman et al. ................ 424/44 |
| 6,506,713 B1 | * | 1/2003 | Slavtcheff et al. ........... 510/130 |
| 2001/0047157 A1 | * | 11/2001 | Burnett et al. .............. 604/289 |

FOREIGN PATENT DOCUMENTS

| EP | 0 409 302 A2 | 1/1991 |
| GB | 2 281 730 A | 3/1995 |
| JP | A 56-164110 | 12/1981 |
| JP | A 10-152428 | 6/1998 |
| RO | 109813 B1 | 6/1995 |
| RO | 116598 B1 | 4/2001 |
| SU | 757161 | 8/1980 |
| WO | 89/03670 | 5/1989 |
| WO | 99/22718 | 5/1999 |

* cited by examiner

*Primary Examiner*—Necholus Ogden
(74) *Attorney, Agent, or Firm*—Young & Thompson

(57) ABSTRACT

This invention relates to a bath composition based on herbs and a foaming agent, in particular a composition including a reagent consisting of sodium bicarbonate and a weak acid such as citric acid which develops carbon dioxide when it comes into contact with water, combined with a surfactant such as lauryl sulphate, and mixed with a quantity of medicinal herbs. When this composition is immersed in the bathwater, the reagent develops a considerable amount of carbon dioxide which, thanks to the surfactant also present in the composition, gives rise to the formation of foam. At the same time, an infusion is obtained due to the presence of medicinal herbs, with the result that the active constituents of the herbs which are dispersed in the water are readily absorbed by the skin through the pores. The invention also relates to packaging in which a quantity of reagent and medicinal herbs is introduced into a bag made, for example, of non-woven fabric.

10 Claims, No Drawings

COSMETIC BATH COMPOSITION BASED ON HERBS AND A FOAMING AGENT, AND PACKAGING CONTAINING THE SAID COMPOSITION

BACKGROUND OF THE INVENTION

This invention relates to a bath composition based on herbs and a foaming agent, in particular a composition including a reagent consisting of sodium bicarbonate and a weak acid such as citric acid which develops carbon dioxide when it comes into contact with water, combined with a surfactant such as lauryl sulphate, and mixed with a quantity of medicinal herbs.

When this composition is immersed in the bathwater, the reagent develops a considerable amount of carbon dioxide which, thanks to the surfactant also present in the composition, gives rise to the formation of foam.

At the same time, an infusion is obtained due to the presence of medicinal herbs, with the result that the active constituents of the herbs which are dispersed in the water are readily absorbed by the skin through the pores. The invention also relates to packaging in which a quantity of reagent and medicinal herbs is introduced into a bag made, for example, of non-woven fabric.

This solution means that the carbon dioxide developed by the reagent in contact with the water is dispersed in the liquid through the openings in the fabric, giving rise to the formation of small bubbles and therefore producing a very fine, lasting foam.

The herbs absorb water and swell, completely filling the bag, which thus turns into a kind of sponge which can be used to rub and massage the skin.

This solution produces a synergic effect between the medicinal herbs and the composition containing the reagent and the surfactant because the foam, possibly aided by a massage with the packaging containing the herbs, aids dilation of the pores and therefore increases absorption of the active constituents of the infusion of medicinal herb, producing a more efficacious effect.

BRIEF SUMMARY OF THE INVENTION

The use of a composition containing a reagent able to develop a gas, in particular carbon dioxide, when it comes into contact with water, combined with a surfactant, is already known.

These compositions are used in the form of granules or spheres which are immersed in the bathwater to form foam, with no need to agitate the water in which the soap or surfactant is dissolved.

However, this system gives rise to the formation of foam with quite large bubbles, which are consequently less stable and lasting.

The use of medicinal herbs to prepare infusions to drink for curative purposes, or to prepare cosmetic compresses and the like for application to the face or skin, is already known.

However, the use of these herbs in cosmetics is limited to this type of application.

The present invention falls into this sector, as it relates to a bath composition comprising a quantity of reagents able to develop carbon dioxide on contact with water, combined with a surfactant designed to cause the formation of foam, and a quantity of dried medicinal herbs which form an infusion in the bathwater containing the active ingredients of the said herbs.

The combination of these two constituents causes a synergic effect, as the cleansing effect of the surfactant and the foam on the skin aids cleansing and dilation of the pores, which consequently absorb the active constituents dispersed in the infusion by the herbs better, and in larger quantities.

In accordance with an advantageous aspect of the invention, these constituents (reagents, surfactant and herbs) are placed inside a bag made of non-woven fabric which aids dispersion of the gas into small bubbles, resulting in the formation of a finer and longer-lasting foam.

Basically, old and new technologies for the manufacture of bath products are combined in the composition in accordance with the invention.

This invention will now be described in detail by reference to the examples illustrated below.

DETAILED DISCLOSURE OF THE INVENTION

As mentioned, the composition in accordance with the invention includes a certain amount of reagent mixed with a surfactant, and a certain quantity of dried medicinal herbs.

The proportions between the two constituents can differ according to preferences, for example depending on whether the aim is to obtain more foam or a higher or lower concentration of the active constituents of the herbs in the bathwater.

These proportions can easily be determined by experts in the field.

The reagent will comprise, for example, sodium bicarbonate associated with a weak acid such as citric acid.

On contact with the bathwater the compound causes the development of a considerable amount of carbon dioxide.

The surfactant, which may be soap, lauryl sulphate or any surfactant used in the cosmetic field, is also dispersed in the water, and the presence of carbon dioxide gives rise to the formation of a large amount of foam.

In accordance with an advantageous aspect of the invention, both the reagent and the dried medicinal herbs will be contained in packaging consisting of a sachet or the like, preferably made of non-woven fabric.

The reagent may be in granule or powder form, and the herbs will preferably be crushed.

The proportions can vary, as mentioned. For example, a pack of suitable size to be conveniently held in one hand could contain 20 grams of reagent and 10 grams of leaves.

Non-woven fabric is particularly suitable to make the packaging, as it has a porosity which promotes the passage of the gas developed during the reaction, but divides it into small bubbles that give rise to the formation of a finer and consequently longer-lasting foam.

The foaming compound can contain the following ingredients, for example:

sodium bicarbonate, citric acid, sodium lauryl sulphate, maltodextrin, silica, perfume, tetrasodium EDTA, PEG-7 gliceryl cocoate, oleth-20 and sodium benzoate.

The perfume could be rose, lavender, pine, sandalwood or any other suitable perfume.

The herbs consist of a mixture of dried medicinal herbs.

By way of example, some mixtures which could be used in the composition in accordance with the invention are set out below, with details of their effects.

| MIXTURE No. 1: NETTLE + DAISY + BRAMBLE | |
|---|---|
| Nettle leaves | 40% astringent/haemostatic/antiseborrhoeic |
| Daisy flowers | 20% refreshing/purifying/softening |
| Bramble leaves | 40% astringent |
| use: | baths for mixed/greasy skin |

| MIXTURE No. 2: EQUISETUM + BIRCH | |
|---|---|
| Birch leaves | 50% toning for greasy or spotty skin, against dermatitis |
| Equisetum tips | 50% diuretic, astringent and wound-healing |
| use: | baths to smooth the skin |

| MIXTURE No. 3: LEMON BALM + CAMOMILE | |
|---|---|
| Lemon balm tips | 40% physical stimulant/antirheumatic |
| Camomile flowers | 60% antineuralgic/decongestant/relaxing |
| use: | relaxing baths |

| MIXTURE No. 4: LAVENDER | |
|---|---|
| Lavender flowers | 100% antiseptic for the urinogenital tract |
| use: | baths for revitalising and disinfecting the skin |

| MIXTURE No. 5: | | |
|---|---|---|
| (bath plants) | Icelandic moss | 40% |
| | calendula flowers | 60% |

When the reagent is completely dissolved, the dried herbs contained in the packaging absorb water and swell, completely filling the bag that constitutes the packaging, thus forming a kind of sponge which can be used to rub and massage the skin.

The abundant foam produced has the effect of a cream on the skin, making it soft and delicate, and ready to absorb the active constituents released by the medicinal plants in the packaging.

The curative effect is performed in three stages.

The foam produced eliminates dead epidermal cells, cleanses the skin deeply, and opens the pores of the epidermis.

When the bag is rubbed over the skin it causes an increase in sub-epithelial blood circulation, at the same time releasing the infusions produced by the herbs.

The plants present, which form an infusion, enable the skin, which is perfectly clean and ready to receive nutrients, to absorb substances that will make it smooth, elastic and velvety.

The cosmetic bath composition thus obtained combines the curative properties of medicinal herbs with the properties of foaming reagents containing soap or surfactant, with a synergic effect.

The packaging of the product can also be used like a sponge to massage the body and the skin, thus improving the effects of the active constituents contained in the herbs.

An expert in the field could devise various modifications and variations, all of which should be deemed to fall within the scope of this invention.

What is claimed is:

1. A bath composition, comprising a reagent that produces a gas upon contact with water and a surfactant, wherein said composition is in a container or fabric material having a porous surface wherein said composition comprises sodium bicarbonate, citric acid, sodium lauryl sulphate, maltodextrin, silica, perfume, tetrasodium EDTA, PEG-7 gliceryl cocoate, oleth-20 and sodium benzoate.

2. The bath composition according to claim 1, further comprising medicinal herbs and wherein said medicinal herbs comprise:

| | |
|---|---|
| Nettle leaves | 40%, |
| Daisy flowers | 20%, and |
| Bramble leaves | 40%. |

3. The bath composition according to claim 1, further comprising medicinal herbs and wherein said medicinal herbs comprise:

| | |
|---|---|
| Birch leaves: | 50%, and |
| Equisetum tips: | 50%. |

4. The bath composition according to claim 1, further comprising medicinal herbs and wherein said medicinal herbs comprise:

| | |
|---|---|
| Lemon balm tips: | 40%, and |
| Camomile flowers | 60%. |

5. The bath composition according to claim 1, further comprising medicinal herbs and wherein said medicinal herbs comprise:

| | |
|---|---|
| Icelandic moss: | 40%, and |
| Calendula flowers: | 60%. |

6. A bath composition, comprising a reagent that produces a gas upon contact with water, a surfactant, and medicinal herbs, and wherein said composition is in a container or fabric material having a porous surface, wherein said composition comprises sodium bicarbonate, citric acid, sodium lauryl sulphate, maltodextrin, silica, perfume, tetrasodium EDTA, PEG-7 gliceryl cocoate, oleth-20 and sodium benzoate.

7. The bath composition according to claim 6, wherein said medicinal herbs comprise:

| | |
|---|---|
| Nettle leaves | 40%, |
| Daisy flowers | 20%, and |
| Bramble leaves | 40%. |

8. The bath composition according to claim 6, wherein said medicinal herbs comprise:

| | |
|---|---|
| Birch leaves: | 50%, and |
| Equisetum tips: | 50%. |

9. The bath composition according to claim 6, wherein said medicinal herbs comprise:

| | |
|---|---|
| Lemon balm tips: | 40%, and |
| Camomile flowers | 60%. |

10. The bath composition according to claim 6, wherein said medicinal herbs comprise:

| | |
|---|---|
| Icelandic moss: | 40%, and |
| Calendula flowers: | 60%. |

\* \* \* \* \*